United States Patent [19]
Wand et al.

[11] Patent Number: 5,051,506
[45] Date of Patent: Sep. 24, 1991

[54] FERROELECTRIC LIQUID CRYSTAL COMPOUNDS CONTAINING CHIRAL HALOALKYOXY TAIL UNITS AND COMPOSITIONS CONTAINING THEM

[75] Inventors: Michael D. Wand; David M. Walba, both of Boulder, Colo.

[73] Assignee: Displaytech, Inc., Boulder, Colo.

[21] Appl. No.: 164,233

[22] Filed: Mar. 4, 1988

[51] Int. Cl.$^5$ .................... C07D 239/72; C09K 19/52
[52] U.S. Cl. .................... 544/289; 544/335; 568/642; 568/643; 560/75; 560/108; 560/109; 252/299.01; 252/299.61; 252/299.66; 252/299.65; 252/299.67; 359/103
[58] Field of Search ............ 252/299.01, 299.61, 252/299.66, 299.65, 299.67; 350/350 S; 560/73, 108, 109; 568/642, 643; 544/298, 335

[56] References Cited

U.S. PATENT DOCUMENTS

| | | | |
|---|---|---|---|
| 4,695,650 | 9/1987 | Walba et al. | 252/299.67 |
| 4,725,688 | 2/1988 | Taguchi et al. | 252/299.61 |
| 4,728,458 | 3/1988 | Higuchi et al. | 252/299.65 |
| 4,798,680 | 1/1989 | Nohira et al. | 252/299.01 |
| 4,831,182 | 5/1989 | Higuchi et al. | 252/299.66 |
| 4,886,619 | 12/1989 | Janulis | 252/299.01 |
| 4,954,600 | 9/1990 | Hachiya | 252/299.01 X |

FOREIGN PATENT DOCUMENTS

| | | |
|---|---|---|
| 255236 | 2/1988 | European Pat. Off. |
| 267585 | 5/1988 | European Pat. Off. |
| 278665 | 8/1988 | European Pat. Off. |
| 62-111939 | 5/1987 | Japan |
| 86/06373 | 11/1986 | World Int. Prop. O. |
| 87/05018 | 8/1987 | World Int. Prop. O. |

OTHER PUBLICATIONS

Walba et al. (1986) J. Amer. Chem. Soc. 108:5210–5221.
Walba et al. (1986) J. Amer. Chem. Soc. 108:7424–7425.

Primary Examiner—John S. Maples
Assistant Examiner—Richard Treanor
Attorney, Agent, or Firm—Greenlee and Associates

[57] ABSTRACT

Chiral, nonracemic compounds of the general formula:

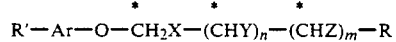

wherein m and n are either both zero, both equal one or n is equal to one and m is equal to zero, X and Y and Z are halogens, R' is an alkyl or alkoxy group having three to fifteen carbons, R is an alkyl group having one to fifteen carbons, and Ar is a 4,4'-substituted phenylvenzoate, 4,4'-substituted biphenylbenzoate, 5,4-substituted 2-phenylpyrimidine or 4,4'-substituted biphenyl core, and wherein * indicates a chiral center, which are useful as ferroelectric liquid crystal components having high polarization are described.

21 Claims, No Drawings

FERROELECTRIC LIQUID CRYSTAL COMPOUNDS CONTAINING CHIRAL HALOALKYOXY TAIL UNITS AND COMPOSITIONS CONTAINING THEM

This invention was made with partial support of the United States Government under Small Business Innovation Research grant numbers F19628-85-C-0087 and F33615-87-C-5293 from the U.S. Air Force. The United States Government has certain rights in this invention.

FIELD OF THE INVENTION

The present invention relates to ferroelectric liquid crystals useful in electro-optical and display device applications.

BACKGROUND OF THE INVENTION

Liquid crystals have found use in a variety of electro-optical and display device applications, in particular those which require compact, energy-efficient, voltage-controlled light valves such as watch and calculator displays. Liquid crystal displays have a number of unique useful characteristics, including low voltage and low power of operation. In such displays, a thin layer of liquid crystal material is placed between glass plates and the optical properties of small domains in the layer is controlled by the application of electric fields with high spatial resolution. These devices are based upon the dielectric alignment effects in nematic, cholesteric and smectic phases of the liquid crystal compound in which, by virtue of dielectric anisotropy, the average molecular long axis of the compound takes up a preferred orientation in an applied electric field. However, since the coupling to an applied electric field by this mechanism is rather weak, the electro-optical response time of liquid crystal based displays may be too slow for many potential applications such as in flat-panel displays for use in video terminals, oscilloscopes, radar and television screens. Fast optical response times become increasingly important for applications to larger area display devices. Insufficient nonlinearity of liquid crystal based displays can also impose limitations for many potential applications.

Electro-optic effects with sub-microsecond switching speeds can be achieved using the technology of ferroelectric liquid crystals (FLCs) of N. A. Clark and S. T. Lagerwall (1980) Appl. Phys. Lett. 36:899 and U.S. Pat. No. 4,367,924. These investigators have reported display structures prepared using FLC materials having not only high speed response (about 1,000 times faster than currently used twisted nematic devices), but which also exhibit bistable, threshold sensitive switching. Such properties make FLC based devices excellent candidates for light modulation devices including matrix addressed light valves containing a large number of elements for passive displays of graphic and pictorial information, optical processing applications, as well as for high information content dichroic displays.

Smectic C liquid crystal phases composed of chiral, nonracemic molecules possess a spontaneous ferroelectric polarization, or macroscopic dipole moment, deriving from a dissymmetry in the orientation of molecular dipoles in the liquid crystal phases (Myer et al. (1975) J. Phys. (Les Ulis, Fr) 36:L-69). The ferroelectric polarization density is an intrinsic property of the material making up the phase and has a magnitude and sign for a given material under a given set of conditions. In ferroelectric liquid crystal display devices, like those of Clark and Lagerwall, appropriate application of an external electric field results in alignment of the chiral molecules in the ferroelectric liquid crystal phase with the applied field. When the sign of the applied field is reversed, realignment or switching of the FLC molecules occurs. This switching can be employed for light modulation. Within a large range of electric field strengths, the switching speed (optical rise time) is inversely proportional to applied field strength and polarization or dipole density (P), and directly proportional to orientational viscosity. Fast switching speeds are then associated with FLC phases which possess high polarization density and low orientational viscosity.

A basic requirement for application of ferroelectric liquid crystals in such devices is the availability of chemically stable liquid crystal materials which exhibit ferroelectric phases (chiral smectic C*) over a substantial temperature range about room temperature. In some cases, the ferroelectric liquid crystal compound itself will possess an enantiotropic or monotropic ferroelectric (chiral smectic C*) liquid crystal phase. Ferroelectric liquid crystal mixtures possessing chiral smectic C* phases with useful temperature ranges can also be obtained by admixture of chiral, nonracemic compounds, designated ferroelectric liquid crystal dopants, into a liquid crystal shot material (which may or may not be composed of chiral molecules). Addition of the dopant can affect the ferroelectric polarization density and/or the viscosity of the C* phase and thereby affect the switching speed. Desirable FLC diopants are molecules which impart high ferroelectric polarization density to an FLC material without significantly increasing the orientational viscosity of the mixture.

Thermotropic liquid crystal molecules typically possess structures which combine a rigid core coupled with two relatively "floppy" tails (see Demus et al. (1974) Flussige Kristalle In Tabellen, VEB Deutscher Verlag fur Grundstoffindustrie, Lebzig for a compilation of the molecular structures of LC molecules). FLC materials have been prepared by the introduction of a stereocenter into one of the tails, thus introducing chirality. The first FLC compound to be characterized was DOBAMBC (Meyer et al., supra) which contains an (S)-2-methylbutyloxy chiral tail. Pure DOBAMBC exhibits a smectic C* phase with a ferroelectric polarization of -3 $nC/cm^2$.

The structures and polarization of several know smectic C* materials, including several containing phenylbenzoate cores, have been summarized in Walba et al. 1986a) J. Amer. Chem. Soc. 108:5210–5221, which also discusses a number of empirical correlations between molecular structure and FLC properties. For example, this reference (and U.S. Pat. No. 4,556,727) reports FLC compounds which contain nonracemic 2-alkoxy-1-propoxy tail units, derived from lactic acid, coupled to 4-substituted phenylbenzoate cores:

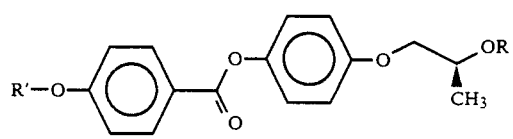

where R is a lower alkyl group containing one to three carbon atoms and R' is an alkyl group containing nine to twelve carbon atoms. These compounds possess monotropic smectic C* phases which display fast switching speeds at room temperature. It is also reported therein that certain eutectic mixtures containing these FLC compounds possess thermodynamically stable or enantiotropic smectic C* phases with high polarization density and fast electrooptical switching speeds.

Walba et al. (1986) J. Amer. Chem. Soc. 108:7424-7425 and Walba and Vohra, U.S. Pat. No. 4,648,073 disclose ferroelectric smectic liquid crystal compounds possessing a high ferroelectric polarization density having chiral tail units derived from (2,3)-alkyloxiranemethanols and achiral phenylbenzoate and biphenyl core units. The ferroelectric crystal materials reported have the following general formulas:

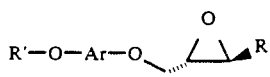

R is an alkyl of one to seven carbon atoms and R' is an alkyl of five to twelve carbon atoms and Ar is phenylbenzoate or biphenyl.

Eidman and Walba, U.S. patent application Ser. No. 800,851, filed July 1, 1986, discloses chirally asymmetric liquid crystals possessing the phenylbenzoate core unit and 1-cyanoalkoxy chiral tails.

Walba and Razavi, U.S. patent application Ser. No. 911,096, filed Sept. 24, 1986 discloses chirally asymmetric compounds possessing a reverse ester phenylbenzoate core unit with 1-fluoro or 1-chloroalkyl group chiral tail units having the general formula:

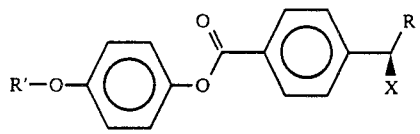

wherein R is an alkyl group of three to twelve carbon atoms, R' is an alkyl of five to twelve carbon atoms, and X is a chlorine atom or a fluorine atom. These materials impart the property of high polarization density in mixtures which display an FLC phase and are useful as FLC dopants.

Walba and Razavi, U.S. patent application Ser. No. 099,074, filed Sept. 21, 1987, discloses chirally asymmetric phenyl and biphenylbenzoates having chiral 2,3-epoxy alkyl or I-halo-2,3-epoxy alkyl tails which are useful as components of FLC materials. The compounds disclosed have the formula:

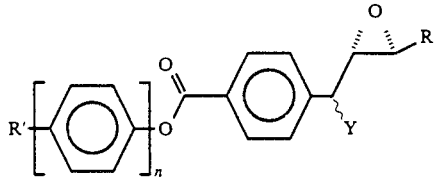

where R' is an alkyl or alkoxyl group having three to fifteen carbon atoms, R is an alkyl group having three to fifteen carbon atoms, n = 1 or 2, and Y is a halogen or hydrogen. It is also disclosed, therein, that 1-haloepoxides of formula A can impart higher polarization densities and higher switching speeds in FLC mixtures than their diastereomers of formula B. It is suggested that the difference in properties of A and B is due to the

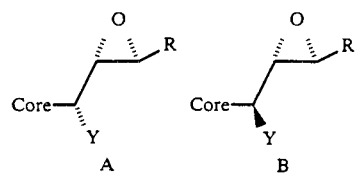

relative alignment of the epoxide and halogen bond dipoles in the isomers.

Higuchi et al. U.S. Pat. No. 4,695,651 disclose biphenyl-based diester liquid crystal compounds having the general formula:

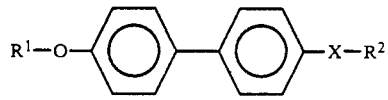

wherein $R^1$ and $R^2$ represent $C_{1-18}$ alkyl, alkyl halide or aralkyl halide groups and X is —COOCH$_2$— or —OCO—. Compounds in Which the $R^2$ group contains an asymmetric carbon are disclosed, although no specific stereochemistry is specified. The liquid crystal materials disclosed are said to display ferroelectricity. In related work, Higuchi et al. U.S. Pat. No. 4,592,858 disclose chiral smectic liquid crystal compounds having biphenyl cores attached by an ester linkage to an optically active group as in the formula:

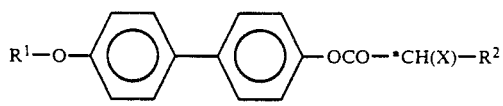

wherein the carbon marked with * is an asymmetric carbon, X is chloro or bromo and $R^2$ is a branched-alkyl group. These compounds are said to exhibit strong ferroelectricity. The stereochemistry of the optically active center is not specified.

Kraus et al. in POT application EP 8,600,248, publication No. WO 8,606,373, disclose optically active nitrogen containing heterocycles which are reported to be useful as constituents for FLC materials. Phenylpyrimidines substituted with optically active groups, including haloalkyl groups are disclosed. The stereochemistry of the optically active centers is not specified.

While several useful ferroelectric liquid crystal materials (both pure compounds and mixtures) have thus bee reported, optimum response times have not been achieved (theoretical limit estimated as 10-50 nsec, Walba et al. (1986a), supra). For this reason, new FLC materials particularly those having high polarization density and low viscosity are desirable, as are new FLC dopants which can impart desired properties to FLC materials. A useful property of FLC dopants is good miscibility in smectic C* matrix materials.

SUMMARY OF THE INVENTION

The present invention provides a class of chirally asymmetric molecules which are useful as components of ferroelectric liquid crystal materials. These compounds can impart the properties of high ferroelectric polarization density and fast electro-optical switching speeds on low polarization materials when mixed with such materials to form ferroelectric liquid crystal compositions. Alternatively, certain of the compounds of the present invention in pure form can also possess stable smectic C* phases having high polarization density.

The compounds of the present invention are prepared by the incorporation of enantiomerically enriched 2-haloalkoxy, 2,3-dihaloalkoxy or 2,3,4-trihaloalkoxy tails into a suitable liquid crystal core (R'-Ar). In general, suitable cores are rigid, linear moieties. Preferred cores are those that are chemically stable and which do not impart high orientational viscosity in the liquid crystal phase. In the present invention cores containing at least one aromatic ring are preferred such as those cores based on a phenylbenzoate, biphenylbenzoate, 2-phenylpyrimidine, or biphenyl structure. The 2-haloalkoxy compounds of the present invention are represented by formula III (Scheme II); the 2,3-dihaloalkoxy compounds by formulas I and II (Scheme I); and the 2,3,4-trihaloalkoxy compounds by formulas IV–VII. More specifically, attachment of these enantiomerically enriched haloalkoxyl tails to the para position of suitable core units results in compounds which are useful in the preparation of ferroelectric liquid crystal materials, either in pure form or as a component in an FLC mixture. Specific core units include: 4-R'-biphenyl

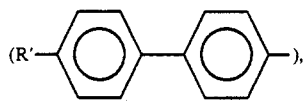

4-R'-phenylbenzoate

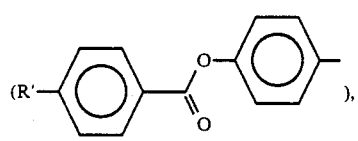

2-(5-R'-phenyl) pyrimidine

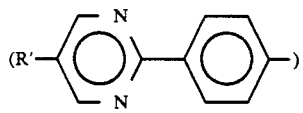

and 4-R'-biphenylbenzoate

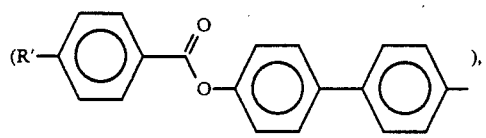

where R' is an alkyl or an alkoxy group having from three to fifteen carbon atoms. The enantiomerically enriched tails of the present invention are incorporated at the para position, with respect of the R' substituent in such cores.

An important feature of the present invention is the finding that the 2,3-dihaloalkoxy compounds of formula I effect much higher switching speeds in FLC mixtures than the analogous diastereomers of formula II. This indicates that compounds of formula I have much higher extrapolated polarization densities than the diastereomers of formula II. This effect is believed to result from the relative alignment of the alkoxy oxygen and halogen bond dipoles in the preferred conformation of the diastereomers in the FLC phase. 2,3,4-trihaloalkoxides of formula IV also effect higher switching speeds in FLC materials than the analogous diastereomers of formulas V–VII, due to an analogous alignment of bond dipoles.

Another surprising finding of the present invention is that the 2,3-dihaloalkoxide regioisomers, as in I, where X is not equal to Y, have significantly different properties in FLC materials. The regioisomers in which F is positioned closer to the core, i.e. in the 2-position, effect higher switching speeds in FLC mixtures than those isomers in which F is further from the core, i.e. in the 3-position. Similarly, 2,3,4-trihaloalkoxide regioisomers of the present invention in which the X substituent is F effect higher switching speeds in FLC mixtures than those trihalide isomers in which F is further from the core.

Specifically, the present invention provides chiral nonracemic mono-, di- and trihaloalkoxides of the formula:

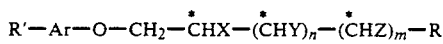

wherein:

Ar is an achiral core unit containing an aromatic ring such as:

4,4'-substituted phenylbenzoate

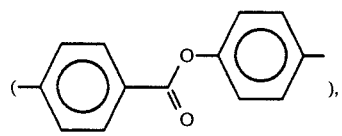

4,4'-substituted biphenylbenzoate

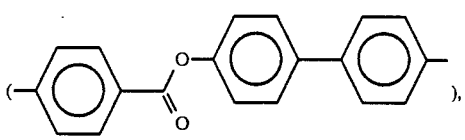

4,4'-substituted biphenyl

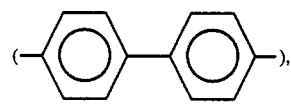

5,4-substituted 2-phenylpyrimidine

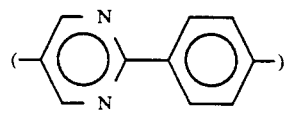

or other functionally equivalent liquid crystal core unit,

R' is an alkyl or alkoxyl group containing three to fifteen carbon atoms, and n and m can be both equal to zero (for monohalides), n can be equal to one and m equal to zero (for dihalides) or n and m can be both equal to one (for trihalides), when n and m are both equal to zero, X is a halide and R is an alkyl group having two to fifteen carbon atoms, when n is equal to one and m is equal to zero, X is a halide, Y is a halide and R is an alkyl group having from one to fifteen carbon atoms, and when n and m are both equal to one, X, Y and Z are halides and R is an alkyl group having from one to fifteen carbon atoms and wherein * indicates an asymmetric carbon. The alkyl and alkoxy groups can be straight chain or branched.

Compounds in which Ar contains two aromatic rings: 4,4'-substituted phenylbenzoate, 5,4-substituted 2-phenylpyrimidine or 4,4'-substituted biphenyl are preferred, the phenylbenzoate and phenylpyrimidine being more preferred. When Ar is a 5,4-substituted 2-phenylpyrimidine it is preferred that R' be an alkyl group having three to fifteen carbon atoms. It is preferred that X, Y and Z are fluorine or chlorine atoms.

More specifically, in one aspect, this invention provides 2-monohaloalkoxides of the formula:

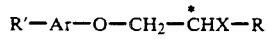

wherein:

Ar is 4,4'-substituted phenylbenzoate, 4,4'-substituted biphenylbenzoate, 5,4-substituted 2-phenylpyrimidine or 4,4'-substituted biphenyl, R' is an alkyl or an alkoxy group having from three to fifteen carbon atoms, when Ar is a 4,4'-substituted phenylbenzoate, 4,4'-substituted biphenylbenzoate or 4,4'-substituted biphenyl or R' is an alkyl group having from three to fifteen carbon atoms when Ar is a 5,4-substituted 2-phenylpyrimidine, X is a halogen, R is an alkyl group having from one to fifteen carbon atoms and wherein * indicates an asymmetric carbon. Alkyl and alkoxy R and R' groups can be straight chain or branched.

Monohaloalkoxides in which Ar is 4,4'-substituted phenylbenzoate, 5,4-substituted 2-phenylpyrimidine or 4,4'-substituted biphenyl are preferred, the phenylbenzoates and phenylpyrimidines are more preferred. For phenylbenzoates and biphenyls, those in which R' is an alkyl or alkoxy group having five to twelve carbons and R is an alkyl group having three to twelve carbon atoms are preferred, and those in which R is an alkyl group having three to seven carbon atoms being more preferred. For phenylpyrimidines those in which R' is an alkyl group having five to twelve carbon atoms and R is an alkyl group having three to twelve carbon atoms are preferred, and those in which R is an alkyl group having three to seven carbon atoms being more preferred. It is preferred that X be a fluorine or a chlorine atom and most preferred that X be a fluorine atom.

In a second aspect, this invention specifically provides chiral nonracemic 2,3-dihaloalkoxides of the formula:

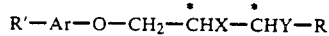

wherein:

Ar is 4,4'-substituted phenylbenzoate, 4,4'-substituted biphenylbenzoate, 5,4-substituted phenylpyrimidine or 4,4'-substituted biphenyl, R' is an alkyl or an alkoxy group having from three to fifteen carbon atoms, when Ar is a phenylbenzoate, biphenylbenzoate or biphenyl or R' is an alkyl group having from three to fifteen carbon atoms when Ar is a phenylpyrimidine, X is a halogen, Y is a halogen, R is an alkyl group having from one to fifteen carbon atoms and wherein * indicates an asymmetric carbon. The alkyl and alkoxy groups can be straight chain or branched.

Dihaloalkoxides in which Ar is 4,4'-substituted phenylbenzoate, 5,4-substituted 2-phenylpyrimidine or 4,4'-substituted biphenyl are preferred; the phenylbenzoates and phenylpyrimidines are more preferred. For phenylbenzoates and biphenyls, those in which R' is an alkyl or alkoxy group having five to twelve carbons and R is an alkyl group having three to twelve carbon atoms are preferred, those wherein R is an alkyl group having three to seven carbon atoms are more preferred, and those wherein R' is n-decyloxy and R is n-propyl are most preferred. For phenylpyrimidines those in which R' is an alkyl group having five to twelve carbon atoms and R is an alkyl group having three to twelve carbon atoms are preferred, those where R is an alkyl group having three to seven carbon atoms are more preferred, and those wherein R' is n-decyl and R is n-propyl are most preferred. It is preferred that X and Y be fluorine or chlorine atoms. It is preferred that X, the 2-substituent, be a fluorine.

In a particular embodiment of the present invention, 2,3-dihaloalkoxides having the structure of formula I are provided, wherein X and Y are halogens, R' is an alkyl or alkoxy group containing three to fifteen carbon atoms, R is an alkyl group containing one to fifteen carbon atoms and the achiral core, Ar, is 4,4'-substituted phenylbenzoate, 4,4'-substituted biphenylbenzoate, 5,4-substituted 2-phenylpyrimidine, 4,4'-substituted biphenyl or other functionally equivalent core. Compounds of formula I will have higher polarization densities than those of their diastereomer of formula II.

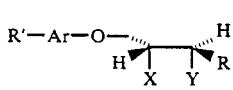 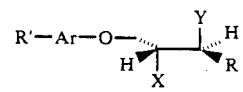

I
[2R,3R]

II
[2R,3S]

Compounds of formula I in which Ar is 4,4'-substituted phenylbenzoate, 5,4-substituted 2-phenylpyrimidine or 4,4'-substituted biphenyl are preferred, phenylbenzoates and phenylpyrimidines are more preferred. For phenylbenzoates and biphenyls, those in which R' is an alkyl or alkoxy group having five to twelve carbons and R is an alkyl group having three to twelve carbon atoms are preferred, those wherein R is a carbon atom having three to seven carbon atoms are more preferred, and those wherein R' is n-decyloxy and R is n-propyl are most preferred. For phenylpyrimidines those in which R' is an alkyl group having five to twelve carbon atoms and R is an alkyl group having three to twelve carbon atoms are preferred, those wherein R is an alkyl having three to seven carbon atoms are more preferred, and those wherein R' is n- decyl and R is n-propyl are most preferred. It is preferred that X and Y be fluorine or chlorine atoms. It is preferred that X, the 2-substituent, be a fluorine.

In a third aspect, this invention provides chiral nonracemic 2,3,4-trihaloalkoxides of the formula:

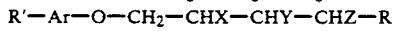

wherein:

Ar is 4,4'-substituted phenylbenzoate, 4,4'-substituted biphenylbenzoate, 5,4-substituted 2-phenylpyrimidine or 4,4'-substituted biphenyl, R' is an alkyl or an alkoxy group having from three to fifteen carbons, when Ar is phenylbenzoate, biphenylbenzoate or biphenyl or R' is an alkyl group having from three to fifteen carbon atoms when Ar is a phenylpyrimidine, X, Y and Z are halogens, R is an alkyl group having from one to fifteen carbon atoms and * indicates an asymmetric carbon. Alkyl and alkoxy R' and R groups can be straight chain or branched.

Trihaloalkoxides in which Ar is 4,4'-substituted phenylbenzoate, 5,4'-substituted 2-phenylpyrimidine or 4,4'-biphenyl are preferred, phenylbenzoates and phenylpyrimidines are more preferred. For phenylbenzoates and biphenyls, those in which R' is an alkyl or alkoxy group having five to twelve carbons and R is an alkyl group having three to twelve carbon atoms are preferred, and those in which R is an alkyl group having three to seven carbon atoms are more preferred. For phenylpyrimidines those in which R' is an alkyl group having five to twelve carbon atoms and R is an alkyl group having three to twelve carbon atoms are preferred, and those in which R is an alkyl group having three to seven carbon atoms are more preferred. Compounds in which X, Y and Z are fluorine or chlorine are preferred. Compounds in which X is fluorine are more preferred.

In a particular embodiment, 2,3,4-trihaloalkoxides having the structure of formula IV are provided, wherein X, Y and Z are halogens, Ar is 4,4'-substituted phenylbenzoate, 4,4'-substituted biphenylbenzoate, 5,4-substituted 2-phenylpyrimidine or 4,4'-substituted biphenyl, R' is an alkyl or an alkoxy group having from three to fifteen carbons, when Ar is phenylbenzoate, biphenylbenzoate or biphenyl or R' is an alkyl group having from three to fifteen carbon atoms when Ar is a phenylpyrimidine, and R is an alkyl group having from one to fifteen carbon atoms. Alkyl and alkoxy R' and R groups can be straight chain or branched. Compounds of formula IV will display higher polarization densities in FLC phases than the corresponding diastereomers (V-VII).

IV

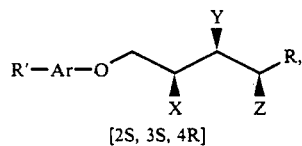

[2S, 3S, 4R]

V

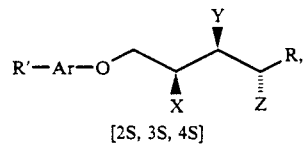

[2S, 3S, 4S]

VI

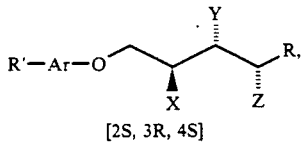

[2S, 3R, 4S]

VII

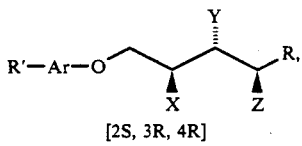

[2S, 3R, 4R]

Compounds of formula IV in which Ar is 4,4'-substituted phenylbenzoate, 5,4-substituted 2-phenylpyrimidine or 4,4'-substituted biphenyl are preferred, phenylbenzoates and phenylpyrimidines are more preferred. For phenylbenzoates and biphenyls, those in which R' is an alkyl or alkoxy group having five to twelve carbons and R is an alkyl group having three to twelve carbon atoms are preferred, and those in which R is an alkyl group having three to seven carbon atoms are more preferred. For phenylpyrimidines those in which R' is an alkyl group having five to twelve carbon atoms and R is an alkyl group having three to twelve carbon atoms are preferred, and those in which R is an alkyl group having three to seven carbon atoms are more preferred. It is preferred that X, Y and Z be fluorine or chlorine atoms. It is preferred that X be a fluorine atom.

DETAILED DESCRIPTION OF THE INVENTION

The ferroelectric liquid crystal compounds of formulas I and II are prepared from chiral 2,3 epoxides according to the general reaction Scheme I. In general terms compounds of formula I are prepared from the chiral nonracemic transepoxides of formula VIII. Initial acid catalyzed epoxide ring opening to give the halohydrin isomers of formulas IX A and B, is followed by stereospecific halogen substitution, which proceeds with inversion at the site of substitution, to give the dihalide of formula I. When X is not the same halogen as Y, two chiral nonracemic regioisomers, I (A and B) are produced. Dihalides of formula II are prepared by analogous methods starting with a chiral, nonracemic cis-epoxide of formula X.

X

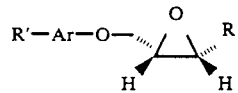

Scheme I

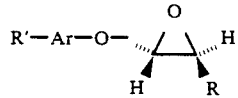

IXA    IXB

-continued
Scheme I

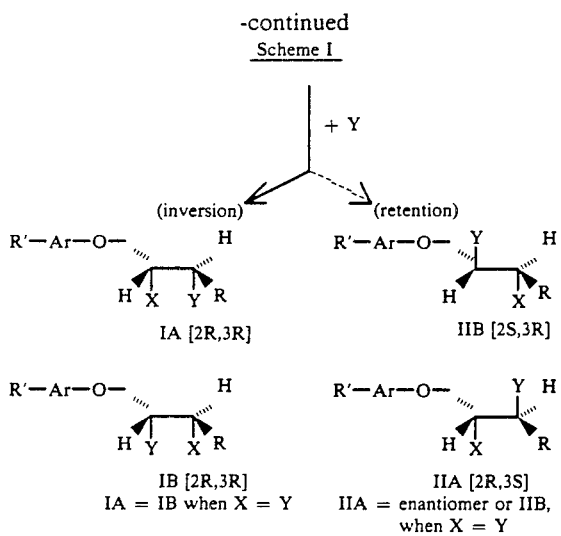

IA = IB when X = Y
IIA = enantiomer or IIB, when X = Y

If the halogen substitution reaction of Scheme I, is only stereoselective, i.e. if a mixture of retention and inversion occurs, then a mixture of diastereomeric dihalides of formulas I and II will result (see Scheme I). In such a case, the resultant mixture of diastereomers can be separated by application of conventional chromatographic techniques.

Compounds of formulas I and II each represent one of a pair of enantiomers. The pair of enantiomers of each compound will function in a complementary manner. For illustration, the structures of the enantiomers of the difluoride (I and I', where X=Y=F) are shown:

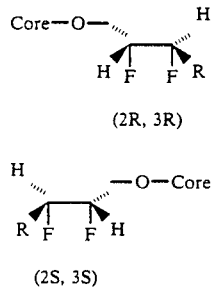

Compound I will function equivalently to its enantiomer of formula I' in FLC materials, except that the sign of P will be reversed. As will be understood by those in the art, the sign of the polarization of an FLC dopant should be the same as that of the host material in order to achieve high polarization mixtures. It is a feature of this invention that either enantiomer of the compounds of formulas I or II can be prepared. This allows choice of the appropriate enantiomer for use with a particular host material. The enantiomers of compounds of formulas I and II can be prepared from appropriate enantiomer of formula VIII or X, respectively, by the methods described herein.

The chiral epoxides of formulas, VIII or X, can be prepared by known methods by coupling of the appropriate chiral epoxy bromides (or in some cases epoxy alcohols) with substituted phenols (XI):

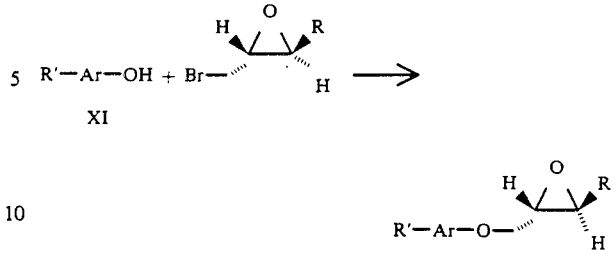

The chiral epoxy bromide (or alcohol) and the substituted phenol starting materials are in turn produced by known methods from readily available starting materials.

The ferroelectric liquid crystal compounds of the present invention having chiral 2-haloalkoxy tails, formula III, can be prepared as exemplified in Scheme II. The synthesis proceeds through a chiral 2-halo alcohol. This halo alcohol intermediate is coupled to a desired core unit by known means as, for example, described herein in the examples. The chiral 2-halo alcohol is made starting with a chiral nonracemic α-hydroxyester (XII), such as D-methyl α-hydroxyisocaproate (where R=iso-propyl). Stereospecific halogenation of the alcohol, for example employing KF or CsCl/18-crown-6 in acetonitrile results in the desired chiral monohalo alcohol intermediate (XIII).

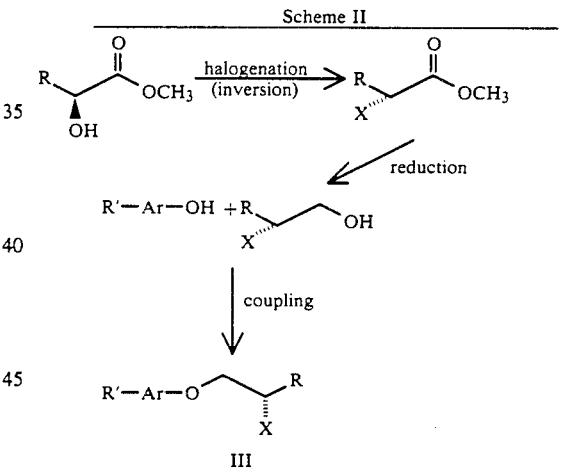

The monohalides of formula III contain a single asymmetric center having two enantiomeric forms, III and III' As noted above both enantiomers will function in an equivalent manner in ferroelectric crystal materials, except that the sign of the polarization of the enantiomers will be reversed.

The ferroelectric liquid crystal compounds of the present invention having chiral 2,3,4 trihaloalkoxy tail units can be prepared as exemplified in Scheme III, for preparation of a trihalide of formula IV. In general, a regioselective Schlosser-Wittig trans olefination (Schlosser, M. et al. (1970) Chem. Ber. 103:2314) is performed on the chiral acetonide of glceraldehyde, in this case on (R)-glceraldehyde acetonide and the resulting product is deprotected with acid to give the substituted chiral trans olefin-1,2(R) diol (XIV). The alkyl substitutent of the diol is selected by use of an appropriately substituted Wittig reagent. Selective protection of the primary alcohol with a hindered reagent, P-Cl in Scheme III, such as trimethylacetyl chloride, followed by stereospecific epoxidation of the olefin, using for example a Sharpless epoxidation with S(+) diethyltartrate (Martin et al. (1981) J. Amer. Chem. Soc. 103:2637), to give an excess of the syn-hydroxyepoxide which is then treated with an SN2-type halogenation agent to result in the chiral haloepoxy protected alcohol (XV). The halo epoxide intermediate is then steroselectively halogenated, as has been described for the epoxides (VIII) in Scheme I, and deprotected to obtain a chiral trihalo alcohols. The trihalo alcohol, which has the 2S,3S,4R stereochemistry results from inversion of configuration with each halogenation (triple inversion). Any retention of configuration, for example on halogenation of the epoxide, results in the production of diastereomers of the 2S,3S,4R trihalo alcohol, as shown in Scheme III. Mixtures of diastereomeric products can be separated using conventional chromatographic techniques. The chiral trihalo alcohols are then coupled to an achiral core unit, R'-Ar-OH, such as the 5-R'-substituted pyrimidine phenol, to give the desired chiral, nonracemic ferroelectric liquid crystal material IV. Coupling to core units is achieved as described in the Examples.

the method of Scheme III, employing the (S)-glceraldehyde acetonide. Replacing the Schlosser-Wittig reaction step in Scheme III with a conventional Wittig reaction results in a cis-olefin intermediate. Starting with the R-glyceraldehyde acetonide, proceeding through the cis-olefin intermediate, followed by stereospecific epoxidation and stereospecific halogenation with inversion results in 2S,3S,4S trihalo alcohol, which on coupling to the core give the compound of formula V. It will be readily apparent to those in the art that each of the compounds IV-VII can be prepared by variation of the stereochemistry of the starting material, choice of regioisomer intermediate and variation in the stereoselectivity of the halogenation reactions in the method described above.

An alternative method can be employed, as shown in Scheme IV, to prepare the chiral trihalo alcohol intermediates and subsequently the ferroelectric liquid crystal materials IV where X, Y and Z are the same halogen. In this method, a nonracemic sugar is converted by a series of reactions to a chiral nonracemic aldehyde bearing protective groups, such as acetate groups (OAc), at the 2,3 and 4 positions. The protective groups are then replaced with halogens by stereospecific or stereoselective halogenation to give a chiral, nonracemic trihaloaldehyde, which can be reduced to give a chiral, nonracemic 2,3,4 trihalo alcohol.

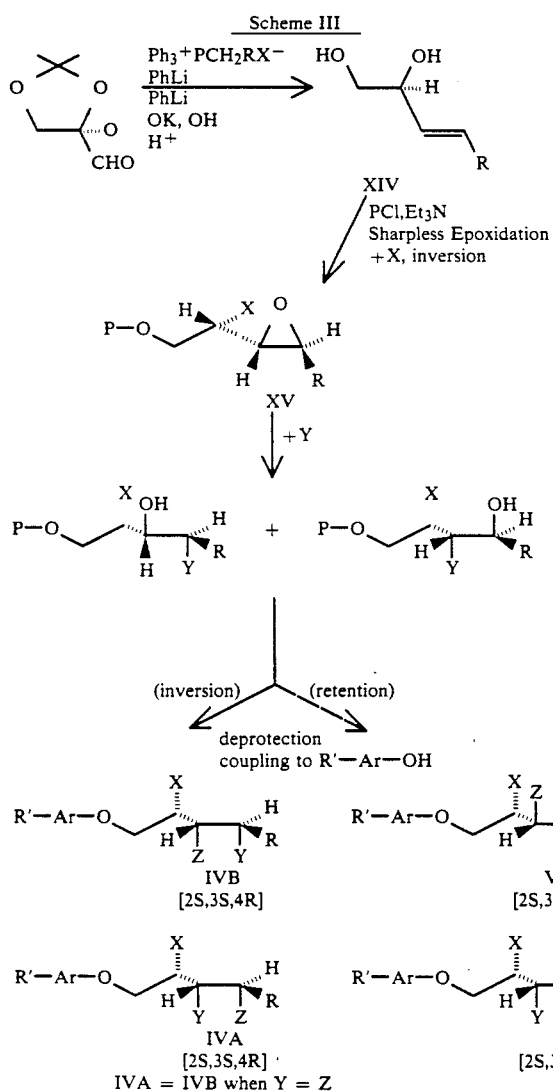

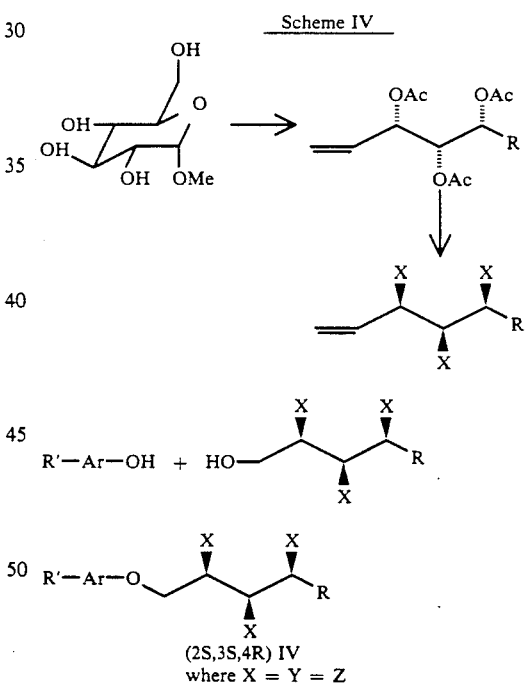

The enantiomer of the 2S,3S,4R trihalo alcohol intermediate, the 2R,3R,4S trihalo alcohol, is prepared by The trihalo alcohol intermediate is then coupled to a desired achiral core unit, for example a phenylpyrimidine, phenylbenzoate, biphenyl or related core, by known methods to produce the compounds of formula IV. For example by coupling of the alcohol intermediate to a 2-phenylpyrimidine core employing DEAD (diethylazodicarboxylate) and triphenylphosphine. Methods analogous to those described in the Examples can be employed to synthesize the analogous biphenyl and phenylbenzoate compounds.

In the method of Scheme IV, the stereochemistry of the trihalo alcohol intermediate is selected by choice of the chiral sugar starting material. Appropriate sugar starting materials are available from commercial sources or can be prepared by conventional methods from known starting materials. For example, the conversion of the α-methyl pyranoside of D-galactose via the reactions of Scheme IV, results in a 2R,3R,4R-trifluoro alcohol and subsequently in the 2R,3R,4R-trifluoroalkoxide which is the enantiomer of compounds of formula V. Similarly, conversion of the α-methyl pyranoside of mannose results in the 2S,3R,4S-trifluoro alcohol intermediate and ultimately in the corresponding compound of formula VI.

Due to the presence of three stereocenters, the trihaloalkoxy compounds of the present invention can have any of four diastereomeric structures: IV-VII. Each of the diastereomers represents two enantiomers. Each pair of enantiomers should function equivalently except with respect to the sign of polarization, as noted above.

The substituted phenols, R'-Ar-OH, employed for the preparation of the compounds of formulas I-VII are either commerically available or can be prepared by methods known to the art.

The liquid crystal properties of the compounds of formula I are exemplified by those of the 2R,3R dihost material, such as W82, mixtures possessing ferroelectric smectic C* phases are produced.

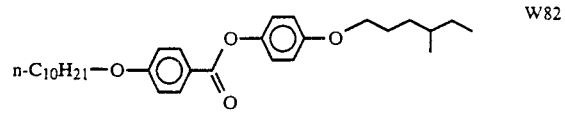

Table 1 summarizes the phase transition temperatures, optical rise times and polarization densities of some exemplary mixtures. In Table 1, the phases are noted as X=crystal, I=isotropic liquid, A=smectic A, C*=smectic C, N*=chiral nematic and phase transition temperatures are given in °C. Optical rise times are measured in response to a driving voltage of 15 V/μm at the temperature given in the table. Polarization densities (P) are given in $nC/cm^2$ and the magnitude of was measured by integration of the dynamic current response on reversing the applied electric field, as described in Martinot-Lagarde (1976) J. Phys. 37, C-3, p.129 and Martinot-Lagarde (1977) J. Phys. Lett. 38, L-17.

TABLE 1

Properties of FLC mixtures

| Mixture | Phase Sequence[1] | $\tau_r$ μsec | Temp. °C. | P $nC/cm^2$ |
|---|---|---|---|---|
| MDW32 + W82 (1:1) | X ← O — I* ← 15 — C* ← 45 — A ← 57 — I | 68 | 30 | 85 ($P_{ex}$ = 170) |
| MDW84 + W82 (10%) | X ← C* ← 58 — A ← 77 — I<br>——— 60 ——→ A — 80 —→ I | 400 | 30 | 0.9 ($P_{ex}$ = 9.0) |
| MDW86 + W82 (10%) | X ← C* ← 74 — A ← 78 — I | 60 | 30 | 12.0 ($P_{ex}$ = 120) |
| MDS88 + W82 (10%) | X ← C* ← 66 — A ← 73 — I | 300 | 55 | |
| MDW89 + W82 (10%) | X ← S₃ ← 30 — C* ← 67 — A ← 72 — I | 46 | 39 | |

[1]transition temperatures are in °C.

chloroalkoxyphenylbenzoate (I, where X Y Cl, R' n-decyloxy, R=n-propyl and Ar=4,4'-phenylbenzoate) which is designated MDW 32, the 2R,3R difluoroalkoxyphenylbenzoate (I, where X=Y=F, R'=n-decyloxy, R=n-propyl and Ar=4,4'-phenylbenzoate) which is designated MDW 86, and those of the regioisomers 2R-fluoro,3R-chloroalkoxyphenylbenzoate (I, where X=F, Y=Cl, R'=n-decyloxy, R=n-propyl and Ar=4,4'-phenylbenzoate) designated MDW 89 and 2R-chloro,3R-fluoroalkoxyphenylbenzoate (I, where X=Cl, Y=F. R'=n-decyloxy, R=n-propyl and Ar 4,4'-phenylbenzoate) designated MDW 88. The liquid crystal properties of the compounds of formula II are exemplified by those of the 2R,3S difluoroalkoxyphenylbenzoate (II, where X=Y=F, R'=n-decyloxy, R=n-propyl and Ar=4,4'-phenylbenzoate) which is designated MDW 84.

The compounds MDW32, MDW 86 and MDW 89, in pure form, do not possess an enantiotropic or monotropic ferroelectric (smectic C*) liquid crystal phase. The compounds MDW 84 and MDW 88, in pure form, possess a monotropic smectic phase, possibly a C phase, that appears to be switchable. The optical contrast of these phases is too low, however, to allow measurement of switching speeds. The low optical contrast of these phases suggests that the tilt angle of the phases is either high (approaching 45) or low (approaching 0°). When any of the compounds MDW 32, MDW 84, MDW 86, MDW 88 or MDW 89 are mixed with a known FLC W82 is known to possess an enantiotropic ferroelectric C* phase with very low polarization density of <0.5 nC cm² and slow electro-optical switching speed of the order of 3 msec (1 μm thick layer, SSFLC geometry, 15 V/μm driving voltage). Mixtures of the compounds of the present invention, particularly compounds as shown in Table 1, possess ferroelectric C* phases with higher polarization density and or faster switching speeds than W82.

An important aspect of the present invention is the finding that the dihaloalkoxides of formula I have properties as FLC dopants significantly different from those of formula II. Compounds of formula I can impart higher polarization densities in FLC mixtures. This property can be qualitatively compared in the different diastereomers by comparing the polarization densities the pure diastereomers would have if they possessed a C* phase, which can be approximately determined by extrapolation from polarization density measurements in mixtures. This difference can be discerned physically, since FLC mixtures containing the I isomer will display higher polarization densities (P), and faster switching speeds than FLC mixtures containing an equal amount of the corresponding II isomer. It is believed that the difference in polarization densities of I and II isomers is due to the relative alignment of the halogen bond dipoles in the preferred conformation of the isomers within the FLC phase. With the I isomers the dipoles are aligned in the same direction with respect to the smectic tilt plane, while in the II isomers the dipoles are opposed, resulting in the higher polarization density of the I isomer. The relationship between dipole alignment and ferroelectric polarization density has been discussed for related molecules in Walba et al. (1986a), and Walba et (1986b), supra. The difference in polarization between isomers of formula I and II is general, dependent on the preferred configuration of the molecule in the liquid crystal phase, but qualitatively independent of X and the structure of the core.

An unanticipated result of the present invention was the finding that the regioisomers of formula I (when X is not equal to Y) can have significantly different properties in an FLC phase. In particular, the isomer in which a fluorine is at the two position, closer to the core linkage, confers a considerable faster switching speed than its analogous regioisomer, in which fluorine is at the three position (see Table 1). The reason for the difference in properties of the regioisomers is not fully understood. The faster switching speeds associated with the 2-fluoro isomers could result from either a lower orientational viscosity or a higher polarization of these isomers.

The high polarization of the monohalides of formula IV are believed to derive from the alignment of the alkoxy oxygen and the halogen bond dipoles in the FLC phase. This alignment can be achieved when the 2-haloalkoxy tail is directly linked to the core unit, by an ether linkage. Similar dipole alignment might not be achieved if, for example, the monohalide alchol tail was indirectly linked to the core, for example by an ester linkage, due to changes in preferred configuration of the tail imposed by the modified linkage and to the presence of other nearby dipoles.

The differences observed between the dihalide diastereomers of formulas I and II indicate that the diastereomeric trihalides (IV–VII) have similar differences in ferroelectric properties. By analogy with the compounds of formula I, compounds of formula IV in which the three halide bond dipoles are aligned with the alkoxy oxygen bond dipole in the preferred configuration are expected to have higher polarization densities, and to effect higher switching speeds than their diastereomers (V–VII).

Variation in the structure of the cores and length and degree of branching in the R and R' groups of compounds encompassed in formulas I–VII can affect the liquid crystal properties of the pure material or mixtures containing them. For example, some of the compounds of the present invention may possess smectic C* phases while others do not and the characteristics of any such smectic C* phases (i.e. stability, temperature range) may vary. Furthermore, the optical switching speed is also affected by the orientational viscosity of the liquid crystal. The structure of the core as well as the size and branching of the R and R groups can affect viscosity. For example, it is expected that compounds of the present invention having phenylpyrimidine cores will show faster switching speeds that their phenylbenzoate and biphenyl analogous due to a lower orientational viscosity associated with the phenylpyrimidine core unit.

Examples

EXAMPLE 1

Synthesis of Phenylbenzoate Epoxides

Chiral nonracemic phenylbenzoate (2,3) epoxides (VIII and X, trans and cis isomers, respectively, where Ar is 4,4'-phenylbenzoate) were synthesized by a modification of the methods described in Walba and Vohra, U.S. Pat. No. 4,648,073. The epoxides are prepared b initial coupling of 4-benzyloxyphenol with an appropriate chiral epoxy bromide, followed by debenzylation of the resulting coupling product and finally by coupling of the resulting substituted phenol with an appropriately substituted alkyl or alkoxy benzoyl chloride:

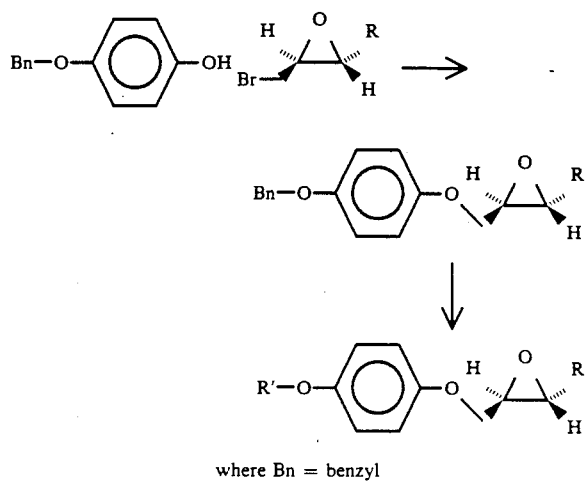

where Bn = benzyl

The epoxy bromides were prepared from the chiral epoxy alcohols described in Walba and Vohra, supra. This example illustrates the procedures for synthesis of phenylbenzoate epoxides by detailing the synthesis of the trans epoxide, 4-[(2S,3S -epoxy]-hexyloxyphenyl-4'-decyloxybenzoate (I, where R'=n-decyloxy and R=n-propyl).

p-Toluenesulfonyl chloride (67.58 g, 0.355 mol) was introduced into a 1 l flame-dried round bottom flask along with 105 ml each of anhydrous THF and dry pyridine. The mixture was stirred until the chloride was dissolved. The resulting solution was cooled to 0° C., after which a solution of (2S,3S)-3-propyloxiranemethanol (39.17 g, 0.338 mol) in 50 ml anhydrous THF was added dropwise. The reaction mixture was then stirred for 18 hr at 5° C. The reaction mixture was then partitioned between water and ethyl ether. The ether layer was removed, washed with dilute HCl and dried with anhydrous MgSO$_4$. Removal of solvent in vacuo gave a pale yellow, oily solid. This material was recrystallized from hexanes affording 70.82 g (72%) of white crystals, the tosylate of (2S,3S)-3-propyloxiranemethanol.

The tosylate (10.8 g, 40 mmol) in 110 ml of anhydrous THF was introduced into a flame-dried 250 ml round bottom flask. Anhydrous LiBr (13.92 g, 160 mmol) was then added to the solution and the reaction mixture was stirred at ambient temperature for 72 hr. THF was then removed from the mixture and the resulting residue was partitioned between water and ether. The ether layer was washed with water, and dried with anhydrous MgSO$_4$. Removal of solvent, at 25° C., 30 torr gave 4.82 g (67%) of 1-bromo-(2S,3S)epoxyhexane as a clear liquid.

4-Benzyloxyphenol (2.0 g, 10.0 mmol) in 50 ml anhydrous THF was added to a 100 ml flame-dried round bottom flask equipped with a condenser. NaH (240 mg, 10.0 mmol) was then added to the flask, after which a solution of 1-bromo-(2S,3S)-epoxyhexane (1.43 g, 8.0 mmol) in anhydrous DMF (10 ml) was added. The resulting reaction mixture was refluxed for 2 hr, after which it was partitioned between water and ether. The ether layer was washed with water and dried with anhydrous $MgSO_4$. Removal of solvent in vacuo, followed by flash chromatography (15% (v/v) ethyl acetate/hexanes) of the residue resulted in 2.01 g (88%) of 4-Benzyloxy-1-[(2S,3S)-epoxy]hexyloxybenzene.

4-Benzyloxy-1-[(2S,3S)-epoxy]-hexyloxybenzene (0.67 g, 2.2 mmol), 5 ml of ethanol and 100 mg of 10% Pd on carbon was added to a glass hydrogenator equipped with a magnetic stir bar. The reaction vessel was then evacuated and hydrogen was introduced. The mixture was allowed to stir for 3-4 hr under a positive pressure of hydrogen until the reaction was complete. The reaction was judged complete by TLC; the product having an Rf=0.28 on elution with 7/3 (v/v) hexanes-/ethyl acetate. The product, 4-[(2S,3S)-epoxy]-hexyloxyphenol (0.35 g), was purified by chromatography employing the same eluent.

To a 10 ml flask equipped with a magnetic stir bar and charged with 4-[(2S, 3S)-epoxy]-hexyloxyphenol (97 mg, 0.5 mmol) was added dry $CH_2Cl_2$ (2 ml), 0.5 ml of triethylamine and a few crystals of DMAP. p-Decyloxybenzoyyl chloride (148 mg, 0.5 mmol) in 1 ml of dry $CH_2Cl_2$ was then added to the flask. The resulting mixture was stirred for 1 hr., after which the solvent was removed. The residue was treated with aqueous HCl (5%, v/v) followed by extraction with ether (2×25 ml). The combined ether layers were washed sequentially with 5% aqueous HCl, 5% aqueous NaOH (2x), and water and then dried over anhydrous sodium sulfate. Removal of solvent gave 0.22 g of crude product, 4-[(2S,3S)-epoxy]-hexyloxyphenyl-4'-decyloxybenzoate (I, where R'=n-decyloxy and R n-propyl), which was then purified by flash chromatography using 9/1 (v/v) hexanes/ethyl acetate as eluent. The product can be further purified by recrystalization from ethanol.

EXAMPLE 2

Synthesis of Chiral Nonracemic 2,3-dihaloalkoxy Phenylbenzoates

This example illustrates the synthesis of chiral 2,3-dihaloalkoxyphenylbenzoates by stereospecific (or selective) halogenation of chiral phenylbenzoate epoxides. These syntheses proceed through 2,3-halohydrin intermediates. The procedure is illustrated by the synthesis of the dichloride, 4 - (2R,3R-dichloro-1-hexyloxy)-4'-decyloxyphenylbenzoate (I, where R'=n-decyloxy, R=n-propyl and X=Y=Cl), the difluoride, 4-(2R,3R-difluoro-1-hexyloxy)-4'-decyloxyphenylbenzoate (I, where R' n-decyloxy, R=n-propyl and X=Y=F) and both of the corresponding 2,3 chloro-fluoro regioisomers, 4-(2R-chloro-3R-fluoro-1-hexyloxy) -4'-decyloxyphenylbenzoate (I, where R'=n-decyloxy, R=n-propyl, X=Cl and Y=F) and 4-(2R-fluoro-3R-chloro-1-hexyloxy) -4'-decyloxyphenylbenzoate (I, where R'=n-decyloxy, R=n-propyl, X=F and Y=Cl).

EXAMPLE 2a 4-(2R,3R-dichloro-1-hexyloxy)-4'-decyloxyphenylbenzoate

To a 50 ml flame-dried round bottom flask equipped with a magnetic stir bar 4-[(2S,3S)-epoxy]-hexyloxyphenyl-4'-decyloxybenzoate (1.87 g, 4.4 mmol) in 15 ml dry THF was added. Lithium chloride (860 mg, 6.4 mmol) and cupric chloride (542 mg, 12.8 mmol) were then added to the solution and the resulting mixture was stirred for 10 minutes at ambient temperature. To the resulting dark brown homogeneous solution, a 1.0M ethereal solution of hydrogen chloride (12.0 ml, 12 mmol) was added. The reaction mixture was then stirred for 18 hours at ambient temperature.

The reaction mixture was worked up with ethyl ether to give 2.07 g of a white solid. TLC of the crude reaction product showed the presence of both chlorohydrin regioisomers. Flash chromatography (7/10/83, v/v/v, EtOAc/$CH_2Cl_2$/Hexanes) afforded 1.524 gm (76%) of pure product, 4- (2S-hydroxy-3R-chloro-1-hexyloxy)-4'-decyloxyphenylbenzoate.

To a 50 ml flame-dried round bottom flask equipped with an argon inlet, a magnetic stir bar and a condenser was added 4-(2S-hydroxy-3R-chloro-1-hexyloxy)-4'-decyloxyphenylbenzoate (505 mg, 1.0 mmol) in 15 ml dry THF. Dry pyridine (1.6 gm, 20 mmol) and thionyl chloride (357 mg, 3.0 mmol) were then added and the reaction mixture was refluxed for 4 hours. Ethereal extractive work up and flash chromatograph (3% (v/v) ethyl acetate/hexanes) afforded 342 mg (67%) of the product, 4-(2R,3R-dichloro-1-hexyloxy)-4'-decyloxyphenylbenzoate as a white solid.

Since this chlorine substitution reaction proceeds with inversion of configuration at the hydroxyl carbon of the chlorohydrin, only the single product 4-(2R,3R-dichloro-1-hexyloxy)-4'-decyloxyphenylbenzoate will result on chlorination of the mixture of chlorohydrin regioisomers (see Scheme I). Separation of the chlorohydrin regioisomers prior to the chlorine substitution reaction is therefore not necessary.

EXAMPLE 2b 4-(2R,3R-difluoro-1-hexyloxy)-4'-decyloxyphenylbenzoate

To a 50 ml polyethylene bottle 4-[(2S,3S)-epoxy]-hexyloxyphenyl-4'-decyloxybenzoate (1.95 g, 4.17 mmol) in 10 ml of dry $CH_2Cl_2$ was added. The reaction solution was then cooled to 0° C., after which 5 ml of $(HF)_x$·pyridine was added and the resulting mixture was stirred for 15 min. The reaction was then quenched by addition of 50 ml of water. Ethereal extractive workup resulted in 1.95 g of a white solid. Flash chromatography of this material (ethyl acetate/hexanes, 15%, v/v) afforded 1.32 g (65%) of a white solid which was a mixture of fluorohydrin regioisomers.

The mixture of fluorohydrin regioisomers (614 mg, 1.26 mmol) in 10 ml of dry $CH_2Cl_2$ was introduced into a 50 ml flame-dried round bottom flask. The solution was then cooled to −78° C., under argon. Diethylamino sulfurtrifluoride, DAST, (175 μl) was added dropwise to the cooled solution which was then stirred for 10 min. The cooling bath was removed after which the reaction mixture was stirred for an additional hour. The reaction was then quenched with 10% (w/v) sodium bicarbonate. A milky white solid was obtained by ethereal extractive workup of the reaction mixture. The product was a mixture of diastereomers: the 2R,3R-difluoro and the 2R,2S-difluoro isomers. The diastereomeric difluorides were separated and purified by flash chromatography (ethyl acetate/hexanes, 8% v/v) in two fractions. The first fraction (175 mg) was the 2R,3S-difluoride. The second fraction (230 mg) was the 2R,3R-difluoride.

Example 2c 4-(2R-chloro-3R-fluoro-1-hexyloxy)-4'-decyloxyphenylbenzoate and
4-(2R-fluoro-3R-chloro-1-hexyloxy)-4'-decyloxyphenylbenzoate The mixture of fluorohydrin regioisomers (600 mg, 1.23 mmol), prepared as in Example 2b, in 15 ml dry THF was introduced into a 50 ml flame-dried round bottom flask equipped with an argon inlet and a condenser. A mixture of thionyl chloride (357 mg, 3.0 mmol) and dry pyridine (800 mg, 10 mmol) was then added to the flask, after which the reaction mixture was refluxed for 4 hr. Ethereal extractive workup of the reaction mixture, followed by gradient elution flash chromatography (1% to 3% v/v, ethyl acetate/hexanes) afforded two major fractions. The first fraction contained 182 mg of the 2R-fluoro-3R-chloro isomer and the second fraction contained 342 mg of the 2R-chloro-3R-fluoro isomer.

A mixture of the 2R-fluoro-3R-chloro and 2R-chloro-3R-fluoro regioisomers can also be prepared by reaction of the chlorohydrin regioisomers, see Example 2a, with DAST fluorination reagent. However, since the DAST reaction proceeds with partial retention of configuration at the hydroxy carbon, two other chloro, fluoro isomers, 4-(2R-chloro-3S-fluoro-1-hexyloxy)-4'-decyloxyphenylbenzoate and 4-(2S-fluoro-3R-chloro-1-hexyloxy)-4'-decyloxyphenylbenzoate are produced.

Example 3

Synthesis of Chiral Dihaloalkoxy Phenylpyrimidines

The chiral 2,3 dihaloalkoxyphenylpyrimidine compounds of formulas I and II (where Ar is 5,4'-phenylpyrimidine) are prepared from the chiral 2,3 epoxy phenylpyrimidines (VIII and X, where Ar=4,4'-biphenyl) using methods analogous to those employed in Example 2.

Chiral phenylpyrimidine epoxides have been prepared by the coupling of substituted pyrimidine phenol with an appropriate chiral bromoepoxide:

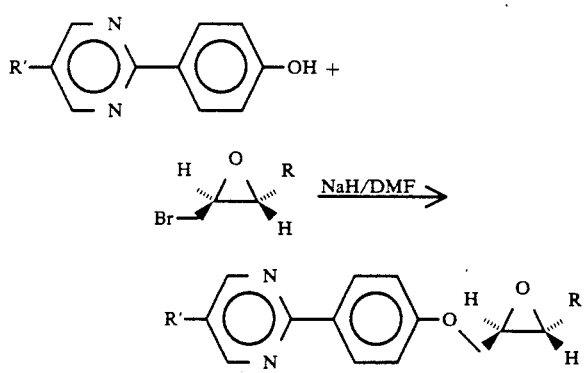

The procedure is illustrated by the preparation of 2-(4-(3-n-propyl(-2S,3S-epoxymethyleneoxyphenyl)-5-decylpyrimidine. A solution of 4-decylpyrimidine-4'-phenol (505 mg, 1.62 mmol) in 10 ml anhydrous THF was introduced into a 50 ml round bottom flask equipped with a condenser. NaH (40 mg, 1.60 mmol) was then added to the flask, after which a solution of 1-bromo-2S,3S-epoxyhexane in 2 ml anhydrous DMF was added. The resulting reaction mixture was refluxed for 2 hr. The reaction mixture was then partitioned between water and ether. The ether layer was washed with water and dries with anhydrous MgSO$_4$. Removal of the solvent in vacuo gave 647 mg of an off-white solid. Flash chromatography (8%, v/v, ethyl acetate/hexanes) of this material followed by recrystalization from hexanes afforded 485 mg of 2-(4-(3-n-propyl)-2S,3S-epoxymethyleneoxyphenyl)-5-decylpyrimidine.

The substituted pyrimidine phenols are prepared by known methods, such as those described in Boller A. et al. (1978) Z. Naturforsch. 33b:433–438.

Example 4

Synthesis of Chiral Dihaloalkoxybiopenyls

The chiral 2,3 dihaloalkoxybiphenyl compounds of formulas I and II (where Ar is 4,4'-biphenyl) are prepared from the chiral 2,3 epoxy biphenyls (VIII and X, where Ar=4,4'-biphenyl) using methods analogous to those employed in Example 2.

The preparation of chiral 2,3 epoxy biphenyls has been described in Walba and Vohra, supra. However, these compounds can also be prepared as described in Examples 1 and 3 by coupling of substituted biphenyl phenols with chiral epoxy bromides. The procedure is illustrated by the synthesis of 4-(3-n-propyl-2S,3S-epoxymethyleneoxy)-4'-decyloxybiphenyl.

A solution of 4'-decyloxy-4-hydroxybiphenyl (342 mg, 1.05 mmol) in anhydrous THF (10 ml) was introduced into a 50 ml round bottom flask equipped with a condenser. NaH (24 mg, 1.00 mmol) was then added to the flask, after which a solution of 1-bromo-2S,3S-epoxyhexane (263 mg, 1.05 mmol) in 2 ml of anhydrous DMF was added. The reaction mixture was then refluxed for 2 hr, after which the reaction mixture was partitioned between water and ether. The ether layer was washed with water, and then dries with anhydrous MgSO$_4$. Removal of the solvent in vacuo resulted in 397 mg (80%) of epoxide VIII, where Ar=4,4'-biphenyl, R'=n-decyloxy and R=n-propyl.

Example 5

Synthesis of Chiral Trihalo Alcohols

The chiral trihalo alcohol intermediates are prepared employing the chiral acetonide of glyceraldehyde and an appropriate Wittig reagent by the method of Scheme III. Alternatively, certain of the chiral trihalo alcohol intermediates (those in which X=Y=Z) can be prepared by the method of Scheme IV starting with an appropriate nonracemic sugar. Both methods are exemplified by the preparation of the 2S,3S,4R trifluoro alcohol, where R is n-butyl.

In the method of Scheme III, (R)-glyceraldehyde acetonide is treated by the regioselective Schlosser-Wittig trans olefination method, employing Ph$_3$P, n-pentyl bromide (or other halogen) and base (i.e. PhLi) and the product is deprotected with acid. The primary alcohol of the resulting trans-olefin diol is selectively protected with trimethylacetyl chloride. Afterwhich the olefin bond of the protected alcohol is steroselectively epoxidized with meta-chloroperbenzoic acid. The resulting epoxy alcohol is fluorinated by initial treatment with mesylchloride/pyridine followed by displacement with KF/18-Crown-6, for example, to give the inversion product, 2(S)fluoro, 3(R)4(R) epoxide. The fluoro epoxide is then treated with HF/pyridine or DAST, with double inversion, to obtain 2(S),3(S),4(R) trifluorononanol, where X=Y=Z and R=n-butyl. Any diasteromeric trifluoro alcohols produced by retention of configuration on halogenation are separated by conventional chromatographic methods.

In the alternative method of Scheme IV, α-methyl D-glucopyranoside is employed as the starting chiral sugar. The sugar is treated with trityl chloride or any other such primary alcohol selective, acid-sensitive protecting group. The remaining free hydroxyl groups of the sugar are then protected for example by acetylation and the resulting protected sugar is treated with acid to produced a hemiacetal. Protection of the aldehyde, for example by Wittig olefination, followed by cleavage of the 1,2-diol with an oxidizing agent such as $RuO_4$ and reduction of the resulting aldehyde with a mild reducing agent, such as $NaCNBH_3$ gives the protected alcohol. Tosylation and alkylcuprate coupling with lithium di(n-butyl)cuprate gives the chiral triprotected alkene. Removal of the protecting groups with mild base or a reducing agent, such as LAH, followed by stereoselective fluorination with DAST reagent, for example, resulting in inversion gives the chiral trifluoroalkene. Ozonolysis followed by reduction of the resulting aldehyde results in 2(S),3(S),4(R) trifluorononanol, where $X=Y=Z=F$ and $R=$n-butyl.

The invention has been described and illustrated by reference to several preferred embodiments, but it is not intended to limit the invention by doing so. For example, in some cases, a single enantiomer of each chirally asymmetric compound has been prepared, it is intended that the invention encompass both enantiomers of each compound. It is also intended that the invention include mixtures of the two enantiomers of the same formula in which there is an excess of one enantiomer. It is further intended that the invention encompass not only the FLC dopant compounds of formulas I–VII, but also compositions or formulations in which these compounds are admixed with each other or with other compounds including LC and FLC materials.

We claim:

1. A chiral nonracemic compound of the formula:

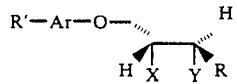

and enantiomers thereof wherein:
X and Y are halogens,
R is an alkyl group containing one to fifteen carbon atoms,
Ar is an achiral core selected from the group consisting of 4,4'-substituted phenylbenzoate, 4,4'-substituted biphenylbenzoate, 5,4-substituted 2-phenylpyrimidine and 4,4'-substituted biphenyl,
when Ar is 4,4'-substituted phenylbenzoate, 4,4'-substituted biphenylbenzoate or 4,4'-substituted biphenyl, R' is an alkyl or alkoxy group containing from three to fifteen carbon atoms, and
when Ar is 5,4-substituted 2-phenylpyrimidine, R' is an alkyl group containing from three to fifteen carbon atoms.

2. The compound according to claim 1 wherein X and Y are fluorine or chlorine atoms.

3. The compound according to claim 2 in which Ar is 4,4'-substituted biphenyl.

4. The compound according to claim 2 in which Ar is 5,4-substituted 2-phenylpyrimidine.

5. The compound according to claim 2 wherein Ar is 4,4'-substituted phenylbenzoate.

6. The compound according to claim 5 in which R' is an alkoxy group containing three to fifteen carbon atoms.

7. The compound according to claim 5 in which R' is an alkoxy group containing three to twelve carbon atoms and R is an alkyl group having three to seven carbon atoms.

8. The compound according to claim 7 in which R' is the n-decyloxy group.

9. The compound according to claim 8 in which R is the n-propyl group.

10. The compound according to claim 9 which is selected from the group of chiral dihalo phenylbenzoates consisting of 4-(2R,3R-dichloro-1-hexyloxy)-4'-decyloxy phenylbenzoate, 4-(2S,3S-dichloro-1-hexyloxy)-4'-decyloxy phenylbenzoate, 4-(2R,3R-difluoro-1-hexyloxy)-4'-decyloxy phenylbenzoate, 4-(2 S, 3 S -difluoro-1-hexyloxy) -4'-decyloxy phenylbenzoate, 4-(2R-chloro-3R-fluoro-1-hexyloxy)-4'-decyloxy phenylbenzoate, 4-(2S-chloro-3S-fluoro-1-hexyloxy)-4'-decyloxy phenylbenzoate, 4-(2R-fluoro-3R-chloro-1-hexyloxy)-4'-decyloxy phenylbenzoate, and 4-(2S-fluoro-3S-chloro-1-hexyloxy)-4'-decyloxy phenylbenzoate.

11. The compound according to claim 1 wherein X is a fluorine and Y is a halogen.

12. The compound according to claim 11 wherein X is a fluorine and Y is a chlorine.

13. The compound according to claim 10 wherein Ar is 4,4'-substituted phenylbenzoate.

14. The compound according to claim 11 which is 4-(2R-fluoro-3R-chloro-1-hexyloxy)-4'-decyloxy phenylbenzoate or 4-(2S-fluoro-3S-chloro-1-hexyloxy)-4'-decyloxy phenylbenzoate.

15. The compound according to claim 1 which has the formula:

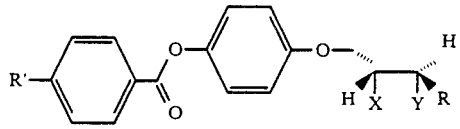

16. The compound according to claim 1 wherein X and Y are both fluorine.

17. The compound according to claim 16 wherein Ar is 4,4'-substituted phenyl benzoate.

18. The compound according to claim 17 wherein Ar has the formula:

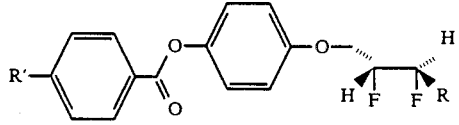

19. The compound according to claim 18 in which R' is an alkoxy group containing from three to fifteen carbon atoms.

20. The compound according to claim 18 in which R is an alkyl group having three to seven carbon atoms.

21. The compound according to claim 18 which is selected from the group of chiral difluoro phenylbenzoates consisting of 4-(2S, 3S-difluoro-1-hexyloxy)-4'-decyloxy phenylbenzoate and 4-(2R, 3R-difluoro-1-hexyloxy)-4'-decyloxy phenylbenzoate.

* * * * *

UNITED STATES PATENT AND TRADEMARK OFFICE
CERTIFICATE OF CORRECTION

PATENT NO. : 5,051,506

DATED : September 24, 1991

INVENTOR(S) : Michael D. Wand and David M. Walba

Page 1 of 4

It is certified that error appears in the above-indentified patent and that said Letters Patent is hereby corrected as shown below: On the title page: Item [54] and Column 1, line 1, rewrite "HALOALKYOXY" as --HALOALKOXY--. In the Abstract, second column, bridging lines 7-8, please rewrite "phenylvenzoate" as --phenylbenzoate--. In the Abstract, line 8, please rewrite "5,4-" as --5,4'--. In the Specification, column 2, line 27, please rewrite "shot" as --host--. At column 2, line 31, please rewrite "diopants" as --dopants--. At column 2, line 48, please rewrite "know" as --known--. At column 3, line 9, please rewrite "4,648,073" as --4,638,073--. At column 3, bridging lines 24-25, please rewrite "patent application Ser. No. 800,851, filed July 1, 1986, discloses" as --Pat. No. 4,777,280, disclose--. At column 3, bridging lines 28-29, please rewrite "patent application Ser. No. 911,096, filed Sept. 24, 1986 discloses" as --Pat. No. 4,695,650, disclose--. At column 3, bridging lines 47-48, please rewrite "patent application Ser. No. 099,074, filed Sept. 21, 1987, discloses" as --Pat. No. 4,835,295, disclose--. At column 3, line 50, please rewrite "I-halo-2,3-epoxy" as --1-halo-2,3-epoxy--. At column 4, line 25, please rewrite "Which" as --which--. At column 4, line 45, please rewrite "Kraus et al. in POT" as --Krause et al. in PCT--. At column 4, line 53, please rewrite "bee" as --been--. At column 5, line 10, please delete "25" preceding "into". At column 6, bridging lines 5-6, please rewrite "2,3,4-trihaloaloxides" as --2,3,4-trihaloalkoxides--. At column 6, circa line 58, please rewrite "5,4-substituted" as --5,4'-substituted--. At column 7, line 15, please rewrite "5,4-substituted" as --5,4'-substituted--. At column 7, line 18, please rewrite "5,4-substituted" as --5,4'-substituted--. At column 7, line 31, please rewrite "5,4-substituted" as --5,4'-substituted--. At column 7, line 37, please rewrite "5,4-substituted" as --5,4'-substituted--. At column 7, line 46, please rewrite "5,4-substituted" as --5,4'-substituted--.

UNITED STATES PATENT AND TRADEMARK OFFICE
CERTIFICATE OF CORRECTION

PATENT NO. : 5,051,506

DATED : September 24, 1991

INVENTOR(S) : Michael D. Wand and David M. Walba

It is certified that error appears in the above-indentified patent and that said Letters Patent is hereby corrected as shown below:

At column 8, line 2, please rewrite "5,4-substituted" as --5,4'-substituted--. At column 8, line 16, please rewrite "5,4-substituted" as --5,4'-substituted--. At column 8, bridging lines 40-41, please rewrite "5,4-substituted" as --5,4'-substituted--. At column 8, line 54, please rewrite "5,4-substituted" as --5,4'-substituted--. At column 9, line 12, please rewrite "5,4-substituted" as --5,4'-substituted--. At column 9, bridging lines 44-45, please rewrite "5,4-substituted" as --5,4'-substituted--. At column 9, line 53, please rewrite "1V" as --IV--. At column 10, line 16, please rewrite "5,4-substituted" as --5,4'-substituted--. At column 10, line 39, please rewrite "transepoxides" as --trans-epoxides--. At column 11, last line, please rewrite "X1" as --XI--. At column 12, circa line 45, please replace the formula:

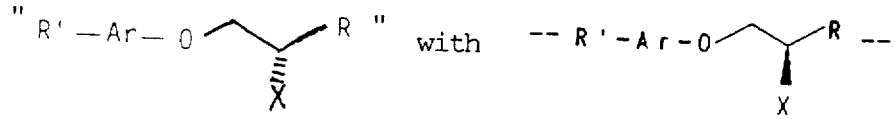

At column 12, line 61, please rewrite "glceraldehyde" as --glyceraldehyde--. At column 12, line 62, please rewrite "glceraldehyde" as --glyceraldehyde--. At column 13, circa line 37, in the formula, please replace:

UNITED STATES PATENT AND TRADEMARK OFFICE
CERTIFICATE OF CORRECTION

PATENT NO. : 5,051,506                           Page 3 of 4
DATED      : September 24, 1991
INVENTOR(S): Michael D. Wand and David M. Walba It is certified that error appears in the above-indentified patent and that said Letters Patent is hereby corrected as shown below:

At column 13, circa line 45, in the formula, please replace:

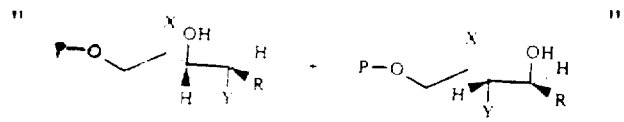

with

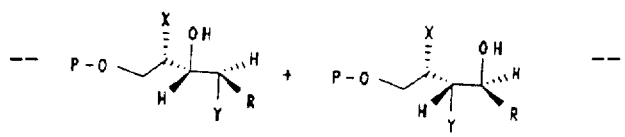

At column 13, circa line 47, please insert --7-- next to the horizontal line of the forked arrow. At column 14, line 1, please rewrite "glceraldehyde" as --glyceraldehyde--. At column 14, in the formulas circa lines 40-50, please insert two arrows between the formulas in the scheme. At column 15, line 40, please rewrite "X Y Cl, R' n-" as --X=Y-Cl, R'=n- --. At column 15, line 50, please insert a comma after "F". At column 16, circa line 18, please rewrite "of was" as --of P was--. At column 16, line 43, please rewrite "0.5 nCcm$^2$" as --0.5nC/cm$^2$--. At column 16, line 48, please rewrite "and or" as --and/or--. At column 17, line 7, please rewrite "et (1986b)" as --et al. (1986b)--. At column 17, line 60, please rewrite "that" as --than--. At column 17, line 60, please rewrite "analogous" as --analogs--. At column 18, line 3, please rewrite "4,648,073" as --4,638,073--. At column 18, line 3, please rewrite "prepared b" as --prepare by--.

UNITED STATES PATENT AND TRADEMARK OFFICE
CERTIFICATE OF CORRECTION

PATENT NO. : 5,051,506
DATED : September 24, 1991
INVENTOR(S) : Michael D. Wand and David M. Walba It is certified that error appears in the above-indentified patent and that said Letters Patent is hereby corrected as shown below:

At column 19, circa line 34, please rewrite "R n-propyl" as --R=n-propyl--. At column 19, circa line 51, please rewrite "R' n-decyloxy" as --R'=n-decyloxy--. At column 21, bridging lines 36-37, please rewrite "4,4'-biphenyl" as --5,4'-substituted 2-phenylpyrimidine--. At column 21, line 59, please rewrite "2-(4-" as --2-(4'- --. At column 21, line 60, please rewrite "4-decylpyrimidine-4'-" as --5-decylpyrimidine-4'- --. At column 22, line 4, please rewrite "2-(4-" as --2-(4'- --. At column 22, line 8, please rewrite "Boller A." as --A. Boller--. At column 22, circa line 13, please rewrite "Dihaloalkoxybipenyls" as --Dihaloalkoxybiophenyls--. At column 23, line 10, please rewrite "produced" as --produce--.

<u>In the Claims</u>
At claim 1, line 9, please rewrite "5,4-substituted" as --5,4'-substituted--. At claim 1, line 15, please rewrite "5,4-substituted" as --5,4'-substituted--. At claim 4, line 2, please rewrite "5,4-substituted" as --5,4'-substituted--.

Signed and Sealed this

Twenty-sixth Day of October, 1993

Attest:

BRUCE LEHMAN

Attesting Officer

Commissioner of Patents and Trademarks